United States Patent
Labyed

(10) Patent No.: US 11,337,679 B2
(45) Date of Patent: May 24, 2022

(54) FREQUENCY SWEEP FOR ACOUSTIC RADIATION FORCE IMPULSE

(71) Applicant: Siemens Medical Solutions USA, Inc., Malvern, PA (US)

(72) Inventor: Yassin Labyed, Maple Valley, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 755 days.

(21) Appl. No.: 15/937,215

(22) Filed: Mar. 27, 2018

(65) Prior Publication Data

US 2019/0298312 A1  Oct. 3, 2019

(51) Int. Cl.
*A61B 8/08* (2006.01)
*A61B 8/14* (2006.01)
*G01S 7/52* (2006.01)

(52) U.S. Cl.
CPC .............. *A61B 8/5269* (2013.01); *A61B 8/14* (2013.01); *A61B 8/5207* (2013.01); *G01S 7/52042* (2013.01)

(58) Field of Classification Search
CPC ....... A61B 8/5269; A61B 8/5207; A61B 8/14; A61B 8/485; A61B 8/54; A61B 8/48; A61B 8/4272; A61B 8/461; G01S 7/52042; G01S 15/8954
See application file for complete search history.

(56) References Cited

U.S. PATENT DOCUMENTS

| | | | |
|---|---|---|---|
| 5,014,712 A | 5/1991 | O'Donnell | |
| 5,142,649 A | 8/1992 | O'Donnell | |
| 5,218,869 A * | 6/1993 | Pummer | G01S 7/52046 600/442 |
| 5,696,737 A * | 12/1997 | Hossack | G01N 29/2462 367/138 |
| 5,891,037 A | 4/1999 | Hossack et al. | |
| 7,066,886 B2 | 6/2006 | Song et al. | |
| 8,002,705 B1 * | 8/2011 | Napolitano | G01S 7/52019 600/437 |

(Continued)

OTHER PUBLICATIONS

Eliana Budelli et al: "A diffraction correction for storage and loss moduli imaging using radiation force based elastography"; Physics in Medicine and Biology; Institute of Physics Publishing; Bristol GB; vol. 62, No. 1; Dec. 14, 2016; pp. 91-106.

(Continued)

*Primary Examiner* — Joseph M Santos Rodriguez
*Assistant Examiner* — Kaitlyn E Sebastian

(57) ABSTRACT

Frequency is swept in acoustic radiation force impulse (ARFI) scanning. Different frequencies are used at different times during the ARFI. For example, different frequencies are focused to different depths in the ARFI transmit beam. Since the frequency sweep is used for the ARFI pushing pulse rather than a transmit pulse for which echoes are received, the rate of change of the frequency is not dictated by the speed of sound. The rate of change of the frequency may be adjustable or set based on other factors, such as the type of tissue. In combination with a time varying focal position, the frequency sweep may better compensate for loss as compared to a focus sweep alone. The frequency sweep may better compensate for loss as compared to a single point focus ARFI.

20 Claims, 4 Drawing Sheets

(56) References Cited

U.S. PATENT DOCUMENTS

| | | | |
|---|---|---|---|
| 8,241,216 B2 | 8/2012 | Loftman et al. | |
| 9,332,963 B2 | 5/2016 | Ivancevich et al. | |
| 2005/0075565 A1* | 4/2005 | Satoh | G01S 15/895 600/437 |
| 2005/0245196 A1* | 11/2005 | Diaz Fuente | H04L 25/0226 455/67.11 |
| 2012/0136250 A1* | 5/2012 | Tabaru | G01S 7/52026 600/438 |
| 2013/0237820 A1* | 9/2013 | Vappou | A61B 8/0858 600/438 |
| 2013/0345565 A1* | 12/2013 | Fan | A61B 8/5207 600/442 |
| 2015/0148651 A1* | 5/2015 | Letovsky | A61N 2/02 600/407 |
| 2015/0201905 A1* | 7/2015 | Ivancevich | G01S 7/52042 600/438 |
| 2017/0245832 A1* | 8/2017 | Kawata | A61B 8/06 |
| 2018/0014814 A1 | 1/2018 | Labyed | |

OTHER PUBLICATIONS

French Search Report dated Feb. 20, 2020 for Application No. FR 1902935.
Zhou, Shiwei, and John A. Hossack. "Dynamic-transmit focusing using time-dependent focal zone and center frequency." IEEE transactions on ultrasonics, ferroelectrics, and frequency control 50.2 (2003): 142-152.

* cited by examiner

FREQUENCY SWEEP FOR ACOUSTIC RADIATION FORCE IMPULSE

BACKGROUND

The present embodiments relate to acoustic radiation force impulse (ARFI) imaging. By transmitting an ARFI pushing pulse, ultrasound may be used to displace tissue directly or through generation of a shear or longitudinal wave. The displacement resulting from the pushing pulse may be measured using further ultrasound scanning. Elasticity, shear, or other types of parametric imaging measure tissue characteristics based on the displacement caused by the ARFI pulse. Tissue with different characteristics responds to displacement differently.

The ARFI pulse is transmitted as a focused beam. The beam has an hour-glass shape with the narrow portion being at the single focus. The beam shape causes a non-uniform response, resulting in less signal-to-noise ratio for displacements measured in some locations. As a result, a limited range of locations are available for measuring tissue characteristics for a given ARFI pulse. To measure over a range of depths, a rapid sequence of separate ARFI pulses focused at different depths is generated. Laterally, the narrow beam width at the focal point limits the lateral extent to which measurements may be applied. ARFI pushing pulses are repeated to measure displacement at different laterally spaced locations. The repetition of ARFI may cause undesired transducer heating and may introduce delays in scanning.

In U.S. Pat. No. 9,332,963, a focus of the ARFI is swept over depth to obtain a more uniform push over depth. As a result, the usable imaging depth span is extended, and image artifacts caused by the hour glass shape of a fixed focus ARFI pulse are reduced. Due to attenuation, the intensity of the ARFI push pulse decreases with depth. Sweeping the focus may not be adequate to compensate for this loss.

SUMMARY

By way of introduction, the preferred embodiments described below include methods, instructions, and systems for swept frequency in acoustic radiation force impulse (ARFI) scanning. Different frequencies are used at different times during the ARFI. For example, different frequencies are focused to different depths in the ARFI transmit beam. Since the frequency sweep is used for the ARFI rather than a transmit pulse for which echoes are received, the rate of change of the frequency is not dictated by the speed of sound. The rate of change of the frequency may be adjustable or set based on other factors, such as the type of tissue. In combination with a time varying focal position, the frequency sweep may better compensate for loss as compared to a focus sweep alone. The frequency sweep may better compensate for loss as compared to a single point focus ARFI.

In a first aspect, a method is provided for swept frequency in acoustic radiation force impulse scanning by an ultrasound system. The ultrasound system transmits from an ultrasound transducer a transmit beam with a frequency sweep as an acoustic radiation force impulse. Different frequencies of the transmit beam are focused at different depths. The ultrasound system, using the ultrasound transducer, tracks displacements of tissue at different depths. The displacement is in response to the acoustic radiation force impulse. An image is generated as a function of the displacement of the tissue at the different depths.

In a second aspect, a system is provided for swept frequency in acoustic radiation force impulse scanning. An ultrasound transducer is for transmitting an acoustic radiation force impulse in a patient. A transmit beamformer is configured to generate waveforms for the acoustic radiation force impulse. The waveforms resulting in the acoustic radiation force impulse have higher frequencies focused to focal zones closer to a transducer and lower frequencies focused to focal zones further from the transducer. A receive beamformer is configured to output data representing spatial locations as a function of received acoustic signals responsive to motion of the tissue due to the acoustic radiation force impulse. A processor is configured to estimate displacement of the tissue in the patient over time as a function of the output data. A display is operable to display an image. The image is a function of the displacement.

In a third aspect, a method is provided for swept frequency in acoustic radiation force impulse scanning by an ultrasound system. The ultrasound system transmits from an ultrasound transducer a transmit beam as an acoustic radiation force impulse where different frequencies of the transmit beam are focused at different depths and have a time varying focal position. The ultrasound system tracks, using the ultrasound transducer, displacements of tissue at different depths. The displacement is in response to the acoustic radiation force impulse. An image is generated as a function of the displacement of the tissue at the different depths.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An ARFI uses a frequency sweep. For example, high frequencies are focused at shallow depths, and low frequencies are focused at deep depths. Since acoustic echoes to the ARFI are not received and processed, the rate of change of the frequency may be based on considerations other than the speed of sound, such as the type of tissue (e.g., different for different attenuation).

In one embodiment, both swept frequency and focus are used for ARFI. Focus and frequency of ARFI push pulse are simultaneously swept. The tissue of interest, size of the region of interest, and position of the region of interest may be used to determine the optimal duration of the ARFI pulse, rates of change of frequency and focus, and/or rate of aperture growth.

The frequency sweep may provide for a more uniform push pulse with depth, limiting signal-to-noise variation and increasing the number of locations available for measuring tissue characteristics in response to a single ARFI. Transducer heating and delays to transmit multiple ARFI to measure tissue characteristics in a region may be avoided. Using both frequency sweep and focus sweep may provide for even greater uniformity, leading to more accurate measurements.

Figure 1:
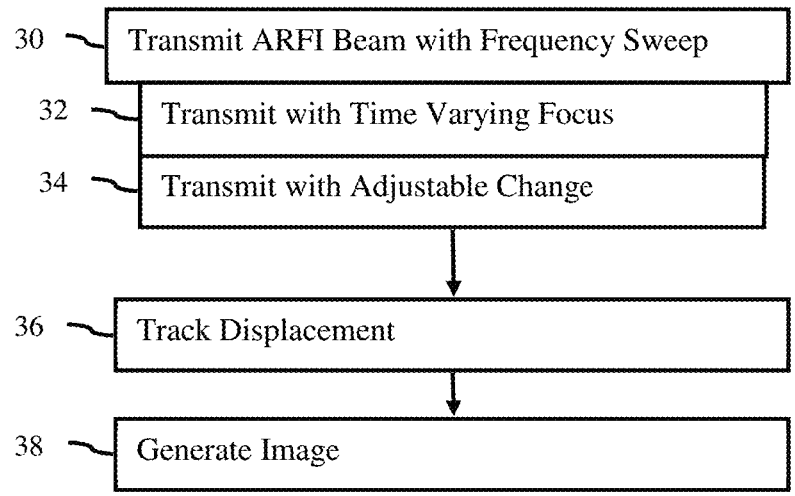
FIG. 1 is a flow chart diagram of one embodiment of a method for swept frequency in acoustic radiation force impulse scanning.

FIG. 1 shows a method for frequency sweep in ARFI scanning by an ultrasound system. An ultrasound transmission is used to generate tissue displacement. By sweeping the frequency of a given ARFI pulse, a single transmit beam provides a more uniform distribution of acoustic energy. Different frequencies attenuate differently, so sweeping the frequency by depth may provide for more uniform distribution for displacing tissue, allowing for greater range of depths and/or for a greater lateral extent over which displacement may be detected.

Figure 6:
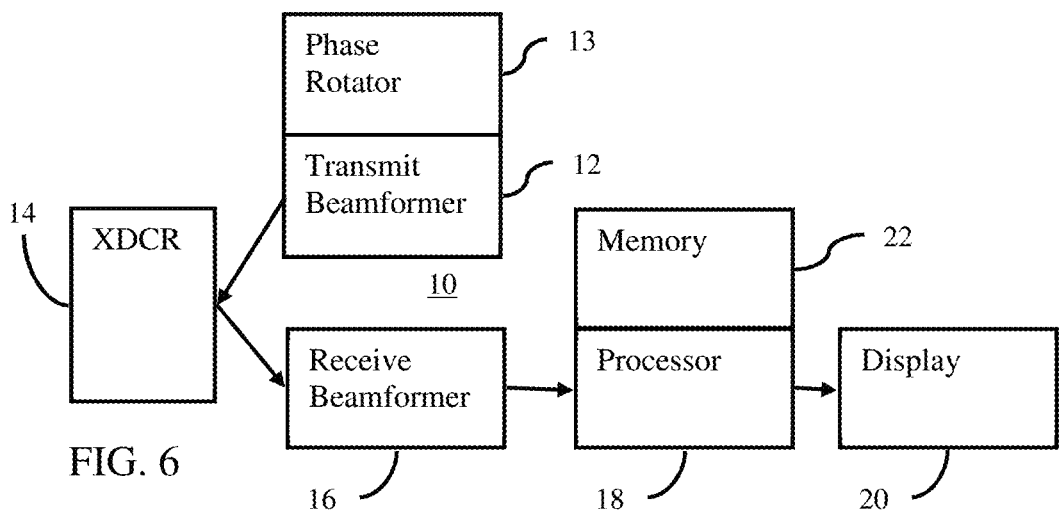
FIG. 6 is one embodiment of a system for swept frequency in acoustic radiation force impulse scanning.

The method is implemented by the system of FIG. 6 or a different system. For example, a transmit beamformer is used to generate element waveforms, and a transducer generates the ARFI transmit beam in response to the element waveforms. The transmit beamformer and a receive beamformer are used to track displacements in tissue caused by the ARFI transmit beam. The ultrasound system generates an image from the displacements.

Additional, different, or fewer acts may be provided. For example, the method is performed without generating an image in act 38. As another example, act 30 is performed without one or more of acts 32 or 34. In yet another example, acts for estimating tissue characteristics or properties from the displacements are provided.

The acts are performed in the order described or shown (e.g., top to bottom or numerical), but may be performed in other orders. For example, acts 32 and 34 are performed simultaneously based on the waveforms generated for the elements of the transducer.

In act 30, an acoustic radiation force impulse (ARFI) beam is transmitted. The beam has a frequency sweep. An array of elements in an ultrasound transducer transmits the ARFI beam converted from electrical waveforms. The acoustic energy with frequency sweep is transmitted to the tissue in a patient.

The acoustic waveform is transmitted for generating a shear, longitudinal, or other wave as stress to displace tissue. The excitation is an ultrasound pushing pulse. The acoustic energy is focused to apply sufficient energy to cause generation of one or more waves travelling through the tissue from the focal location or locations. The acoustic waveform may itself displace the tissue.

The shear wave or waves are generated at the focal region and propagate laterally, axially, and/or in other directions from the focal region. The waves may travel in multiple directions. The waves reduce in amplitude as the waves travel through the tissue.

To generate the wave, high amplitude or power excitations are desired. For example, the excitation has a mechanical index of close to but not exceeding 1.9 at any of the focal locations and/or in the field of view. To be conservative and account for probe variation, mechanical index of 1.7 or other level may be used as the upper limit. Greater (e.g., MI exceeding 1.9) or lesser powers may be used.

The waveforms applied to the elements are generated as continuous waveforms. The waveforms vary, such as being square wave, sinusoidal waves, or other unipolar or bipolar alternating waveforms. The waveform does not have any extended periods of zero output other than to begin and end the waveform. An extended period is one or more cycles. There may be part of each cycle at zero, such as for a unipolar square wave, but another part of the cycle has non-zero (positive or negative) output per cycle.

The ARFI beam is transmitted with waveforms having any number of cycles. In one embodiment, one, most, or all the waveforms for a transmit event have 100-2,000 cycles. The number of cycles is tens, hundreds, thousands, or more for the continuous transmit waveforms applied to the elements of the array for the ARFI beam. Unlike imaging pulses that are 1-5 cycles, the ARFI pushing pulse has a greater number of cycles to generate sufficient stress to cause the wave (e.g., shear wave) for displacing tissue with an amplitude sufficient to detect. A pushing pulse beam of acoustic energy is transmitted. ARFI is transmitted from the array by application of the continuous transmit waveforms to the elements of the array over the period.

The length of the transmission in combination with the amplitude provides acoustic power to the tissue. This power may cause a rise in temperature in the tissue. Transmitting along the same or adjacent scan lines may cause the tissue to increase in temperature over time. Biological effects may include hyperthermia at tissue temperature of about 41-45° C., protein denaturation at temperatures above 43-45° C., and tissue necrosis at temperatures above 50° C. Tissue stiffness may be affected even at temperatures below 43-45° C. At temperatures above 43-45° C., increases in viscosity and/or stiffness may occur. At temperatures above 50° C., the tissue may have a high stiffness and/or high attenuation. Biological effects are limited by preventing a temperature increase of over 2 degrees Celsius. Alternatively, the transmissions may cause biological effects.

By using a swept frequency with a swept focus, a broader region is subjected to tissue displacement for each ARFI beam, resulting in less temperature rise for the transducer and/or the tissue to scan a given region of interest. The excitation is focused at a plurality of locations to allow detecting of the resulting shear wave or waves over a broader range of depths in tissue of interest (e.g., tissue region surrounding and/or including a possible tumor). Focusing different frequencies at different depths may allow for sampling displacements in a broader region of tissue than using a single focus or single frequency over a time varying focus.

The ARFI beam is generated with constant amplitude modulation. In an alternative embodiment, the amplitude of the transmit beam is varied over time with the frequency change. For example, greater amplitudes are provided for focal locations at deeper depths. The amplitudes of the electrical waveforms applied to the elements to generate the beam vary as a function of time over the period. The variation rate is constant but may vary.

The ARFI beam is generated with a constant aperture. For example, all 128 or 256 elements are used for each frequency. In other embodiments, the aperture size (e.g., channel mask) varies with the time varying frequency. To maintain constant F #, the size of the aperture may increase or decrease based on frequency. Some elements are used for some but not all frequencies of the sweep. The aperture may be smaller (e.g., fewer number of elements) for lower frequencies and larger for higher frequencies.

Figure 2:
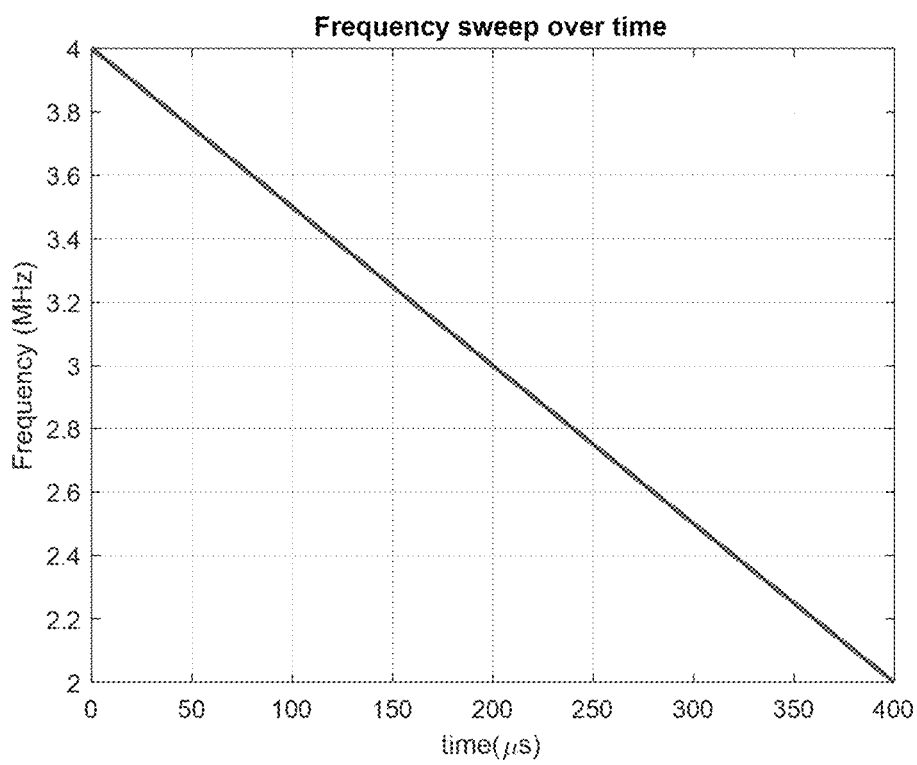
FIG. 2 is an example frequency as a function of time for a frequency sweep in ARFI.
Figure 3:
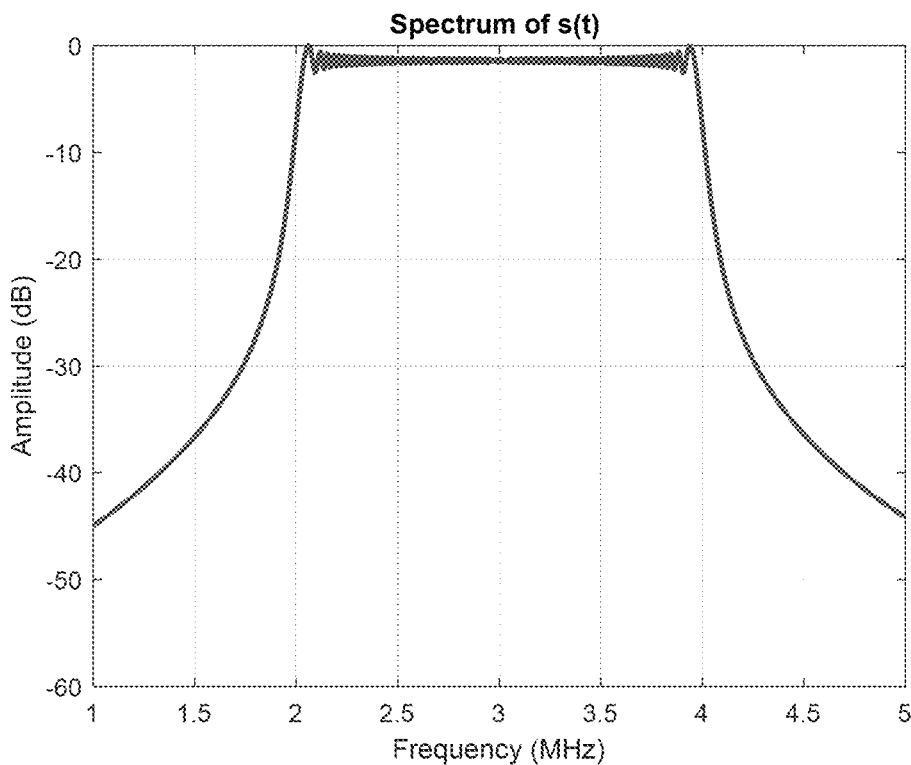
FIG. 3 is an example spectrum of a waveform signal at an element for generating a transmit beam with the frequency sweep of FIG. 2.

The ARFI transmit beam has a frequency sweep. During the period of transmission, the frequency content changes. For example, a center frequency for an initial cycle is different than the center frequency for a last cycle. In one embodiment, a chirp is used where the frequency changes linearly with time. FIG. 2 shows an example. In other embodiments, a non-linear frequency sweep over time is used. Stepped or variation in slope of the frequency as a function of time may be used. Similarly, the frequency band shifts over time. The range of frequencies, the lowest frequency, and/or the highest frequency varies over time during the continuous ARFI transmission. Any measure for the edge of the band may be used, such as 10 or 20 dB down from a peak.

The same frequency sweep is provided for each of the element waveforms. Each element transmits acoustic energy at a same or similar (e.g., within 5%) center frequency at the same or different times. Where the focus is fixed, the relative delay or phasing dictates the frequency for each element so that the acoustic energy generated by the element has a same or similar frequency when converging at the focal location. Where the center frequency for the elements varies over time, the frequency of the transmit beam at the focal location or locations also varies over time. The frequency sweep is implemented by the transmit beamformer changing the frequency of pulsing by pulsers and/or by generation of the waveforms having the frequency sweep. For the transmit beam generated in response to application of the waveforms to the transducer, the frequency at the focal location or locations of the transmit beam varies over time.

In combination with a swept focus, the transmit beam of the ARFI has different frequencies transmitted to different depths. Different center frequencies are transmitted to different depths. As the frequency changes over time in the frequency sweep, the focal depth varies in a time varying focus. Successively higher frequencies are focused to successively closer focal zones, or vice versa. Any range of locations and/or range of frequencies may be used. The change in focal depth over time may result in change in the relative frequency between element waveforms so that the desired frequency is provided at the desired focal location.

The focus for generating the wave or waves is swept in act 32. To sweep the focus, the location of the focus is changed over time. A given ARFI transmission occurs over a period. One or more elements begin outputting acoustic energy first and others join at different times based on relative delay or phasing. The waveforms for each element continue, with some ending before others end. This period is for one beam or pushing pulse transmission and extends from the time at which the array starts generating acoustic energy and ends at the time at which the array then ceases generating acoustic energy. The sweep in focus and/or frequency sweep occurs during the period for generating a given transmit beam.

The excitation is focused using a phased array with or without a mechanical focus. A mechanical focus may be provided for a given direction, such as an elevation focus. Azimuth and/or axial mechanical focus may be provided. In at least one direction and possibly all three (e.g., axial, azimuth, and elevation), the array of elements is electronically focused. The electronic focus allows variation of the focus during the period. The sweep of the frequency occurs in the waveforms applied to each element.

The time varying focus may have a line focus. The line is straight or curved. The line is continuous but may be for multiple discrete regions (not continuous). The focus changes position over the period during which the transmit beam is generated.

To sweep the focus, the phase profile, delay profile or both are altered over the period in act 32. Other approaches for sweeping the focus may be used. For transmitting a beam with a single focal point, the phase profile is constant in time. During the period, the same relative phase between the waveforms of the different elements is used. For a swept focus, the phase profile across the array varies during the period. The amount of relative phase difference between two or more waveforms of elements of the array changes. The phase is changed differently for some waveforms and corresponding elements than for others. To focus at a different location, a different phase profile is used. The phase profile is different by having different relative delays between the elements. In sweeping the focus to move the focal location, the different delay profiles are implemented. At different times in the period, different relative phasing is applied.

As a given waveform for a given element is generated, the phase relative to other waveforms changes. A phase rotator or delay adjustment may be used. Alternatively, the waveform is generated with the variance in relative phase or delay. The changes in relative phases or delays across the array cause parts of the respective waveforms to be focused at different locations. The focus for the transmit beam varies during the period for which the beam is generated. The waveforms are generated and/or applied to the transducer to include both the variation to sweep the focus and the frequency sweep.

Any change function may be used for the phase or delay. In one embodiment, the phase profiles constantly change over time. The change occurs every N clock cycles of the transmit beamformer wherein N is an integer. N may be 1 for constant change. For less frequent change, N may be a greater number. In other approaches, constant change is provided with N greater than one but sufficient to cause less than 2 dB down from the peak along a continuous focal region.

Depending on the focal locations, the phase for one or more waveforms and/or elements may not change at all or not change for a number of clock cycles. For example, the phase applied to the waveform for a center element of an array where the focus is swept axially along a normal to the array may be the same for the entire period. Phases for the waveforms of elements at the ends of the aperture may have the greatest variance and rates of change. For the array, the one or more phase terms are constantly changing.

The phase change may be implemented using a phase rotator. In one embodiment, the phase is controlled using different phase terms, such as constant phase, linear phase, and quadratic phase terms. Additional, different, or fewer phase terms may be used. To maintain the same relative phase for a single focal point, the phase terms are constant in time. To sweep the focus, one, more, or all the phase terms may vary over time. The phase terms for a swept focus are channel and time dependent rather than just being channel dependent for a single focus location.

The rate of change in the phase profile or phase for given elements is constant. The rate may be different for different elements depending on the steering angle and the element position within the aperture. In other embodiments, the rate of change in phase varies. For example, the rate of change may be slower for some range of focal locations to increase the dwell time or amount of acoustic energy transmitted while focused in that region or range of locations. The rate of change may be zero for some focal locations, at least for a part of the period. The focal position may vary over time with discrete steps in position rather than constant variance.

A single transmit beam is transmitted with the time varying focal position and frequency sweep. In other embodiments, a given transmit event may form more than one beam (e.g., simultaneous multi-beam). One, some, or all the transmit beams have time varying foci and frequency sweep. Whether transmitting a single beam or multiple beams during a given transmit event, the transmission event occurs over a period of uninterrupted generation of acoustic energy by the array. At least one element is generating acoustic energy at any point during the period. Subsequent beams may be formed in a non-continuous manner, such as by having a period of one or more waveform cycles without any of the elements of the array generating acoustic energy. Non-continuous may be based on most of the elements or other number of elements not generating acoustic energy.

The focal position and corresponding frequency varies axially, laterally or axially and laterally. The time varying focal position and frequency varies by axial position.

In one embodiment, the frequency sweep is provided by generating the element waveforms having the frequency sweep and relative delaying or phasing of the waveforms by delays or phase rotators for application to the transducer. In another embodiment, the element waveforms are generated to provide both the frequency sweep and the time varying focus. For example, assuming focus and frequency change linearly with time, then the ARFI pushing pulse is represented as:

$$s(t) = \sin(\omega_{max} t + 0.5\alpha t^2) \quad (1)$$

where t is time, $\omega_{max}$ is the maximum angular frequency, and $\alpha$ is a rate of change in the angular frequency. For a pulse duration of $\Delta t$, the rate of change in the frequency is:

$$\alpha = \frac{\omega_{min} - \omega_{max}}{\Delta t}. \quad (2)$$

Other functions may be used for the rate of change, including linear or non-linear. A constant or time varying rate may be used. The time-dependent focus is represented as:

$$F(t) = \frac{d_{max} - d_{min}}{\Delta t} t + d_{min} = \beta t + d_{min} \quad (3)$$

where d is the depth, and $\beta$ is a rate of change for the focus. Other functions may be used for the rate of change, including linear or non-linear. A constant or time varying rate may be used.

The time-dependent delay of each transducer element i at azimuth position $x_i$ on a linear array, where i goes from 1 to L, is given by:

$$\tau(t, x_i) = \frac{\sqrt{F(t)^2 + x^2} - F(t)}{c}. \quad (4)$$

s(t) of equation 1 may be rewritten as:

$$s(nT, x=0) = \Sigma_{n=0}^{N-1} \sin(\omega_{max} nT + 0.5\alpha(nT)^2))\delta(t-nT), \quad (5)$$

where n is an index, $\delta$ is the Kronecker delta function, and T is a period between two delta functions. Other delay or phasing functions may be used. The delta function introduces the relative delay and/or phasing into the waveform for each element. The transmitted waveform on each element is given by:

$$s(nT, x=x_i) = \Sigma_{n=0}^{N-1} \sin(\omega_{max} nT + 0.5\alpha(nT)^2))\delta(t-nT+\tau(nT, x_i)) \quad (6)$$

Other functions may be used, such as to account for curvature in the array. The sine function term provides the frequency sweep, and the Kronecker delta function term provides the corresponding time varying focus.

The waveform generated for each element in the aperture are square waves or sinusoidal waves. The generated waveforms are applied to the elements in synchronization, resulting in generation of the ARFI transmit beam with frequency and focus sweeps.

The rate of change in the frequency and/or the rate of change of the time varying focus may be adjustable. Different settings may be used. For example, one setting for the rate is used for one type of tissue and another setting is used for another type of tissue. The size of the region of interest (i.e., ARFI scan region) and/or position of the region of interest may also or alternatively be used to set the rate. The same or different information may be used to set the rate of change in frequency and the rate of change in time varying focus. Attenuation and/or other information may be used.

Where the transmit beam is used to receive responsive echoes, then the rate of change corresponds to the speed of sound. In dynamic receive focusing, the focal position changes with the speed of sound. To align the transmit and receive focus, then the transmit focus and corresponding frequency sweep changes with the speed of sound. Since ARFI is used to cause tissue displacement and not to receive responsive echoes, the adjustable rates may be different than the speed of sound. For example, the rate of change in the frequency may be 100 m/s, which is different than the speed of sound, 1,540 m/s, by a factor of 10. Other differences may be used.

Since the rate is adjustable, various linear or non-linear functions may be used. Equation 2 above is one example. Since the rate is adjustable, the rate may be set based on input from the user. For example, the user selects an application. The application indicates the type of tissue. Different tissues have different attenuation and/or absorption as a function of frequency. The rate of change in the frequency and the focal position are set based on the selected application. As another example, the position and/or size of the region of interest (e.g., region in which shear wave is to be imaged) are input by the user. The range of frequencies and focal positions may relate to the size of the region of interest. The position of the region may determine the minimum and/or maximum frequencies and/or focal positions. The rate of change in the frequency and/or focal position are set based on the region of interest size and position. In yet another example, the user directly selects a setting for the rate, such as selecting a rate value. The user input rate value is used instead of equation 2 or is used to then set the maximum and minimum frequencies to provide the selected rate.

Figure 4:
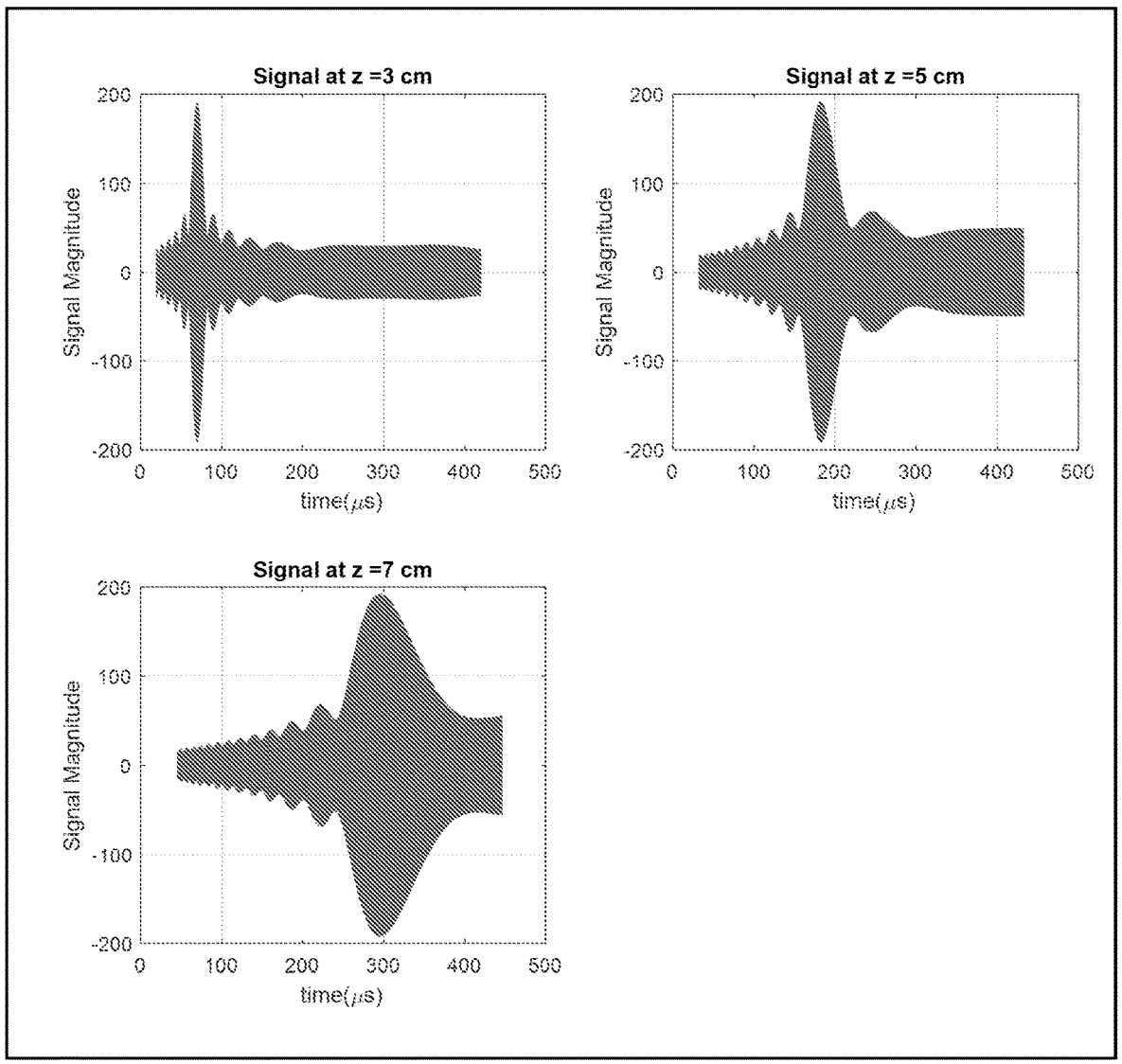
FIG. 4 shows example signal magnitude as a function of time for an ARFI transmit beam with swept frequency and time varying focus.
Figure 5:
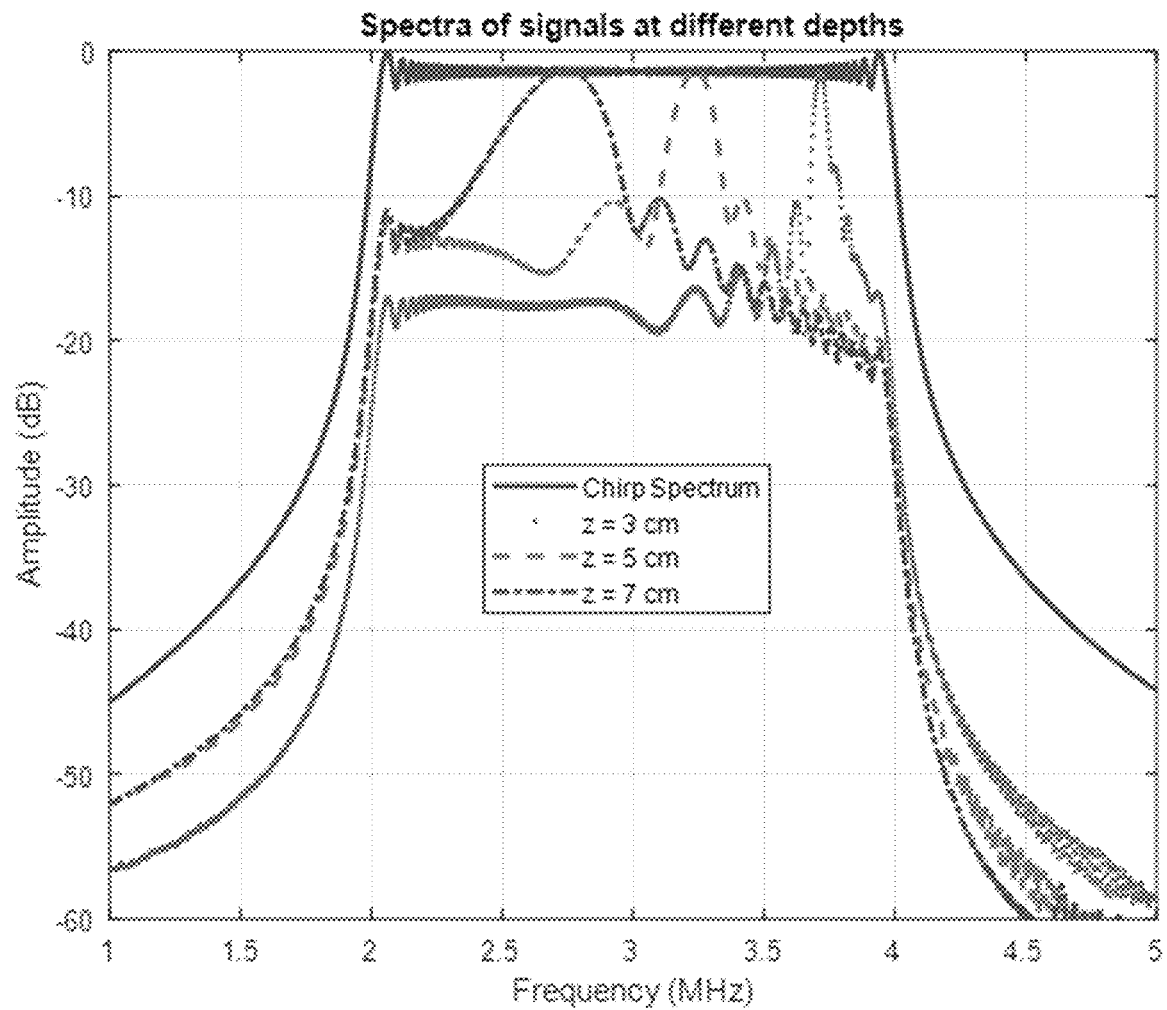
FIG. 5 shows the spectra of the signals from FIG. 4.

FIGS. 4 and 5 show example transmit beams generated from element waveforms based on equation 6. The ARFI pulse duration $\Delta t = 400$ μs. The frequency changes from $f_{max} = 4$ MHz to $f_{min} = 2$ MHz. The initial focus is $d_{min} = 2$ cm and final focus $d_{max} = 10$ cm. As a result, the rate of change in the frequency $$\alpha = \frac{\omega_{min} - \omega_{max}}{\Delta t} = -\pi 10^{10} (1/s^2),$$

and the rate of change in focal depth $$\beta = \frac{d_{max} - d_{min}}{\Delta t} = 200 \text{ (m/s)}.$$

FIG. 4 shows the ARFI signal of the transmit beam at different depths (e.g., 3, 5, and 7 cm) as a function of time. The transmit beam is generated using frequency sweep and time varying focus. Different frequencies are transmitted to different depths. While not possible to visualize the frequency of oscillation with time due to the long duration of the pulse in FIG. 4, a chirp with maximum energy at the frequency of interest (e.g., high frequencies at shallow depths and low frequencies at deep depths) are provided. FIG. 5 shows the spectra of the signals of FIG. 4. In FIG. 5, the spectra show that at a particular depth, the majority of the push energy is concentrated in a narrow frequency band. FIG. 4 represents the same information as FIG. 5, but in the time domain. Due to attenuation and/or diffraction, the amplitude of the signals at the different depths is different. Amplitude modulation may be used to make the amplitudes more similar.

In act 36, the ultrasound system, using the beamformer, transducer, and an image processor, tracks displacements in the tissue caused by the wave generated from the ARFI transmit beam. The beamformer generates transmit waveforms, the transducer converts the waveforms to transmit beams and converts echoes of the transmit beams to receive signals, the beamformer forms receive beams from the receive signals, and the image processor correlates receive beams or data from the receive beams to determine displacements.

The tissue response is a function of the wave created by the ARFI beam and the tissue characteristics. The displacement of the tissue over time may be expressed as a convolution of the waveform and the tissue characteristics or response. The tissue response reflects viscoelastic properties of the tissue. To measure the viscoelastic properties, the displacement of the tissue over time in response to the pushing pulse is measured. The displacement of the tissue caused by the created wave or the ARFI pulse itself is determined over time. As the wave passes a given location, the tissue displaces by an amount or distance that increases to a peak amount and then decreases as the tissue returns to rest.

In act 36, the displacement is calculated as a function of time. The tissue is scanned multiple times to determine the displacement, such as scanning a region at least ten times to determine displacements at nine different times. The tissue is scanned using any imaging modality capable of scanning for displacement during the tissue's response to the pushing waveform. The scan occurs over a range of times where the desired waveform (e.g., shear wave) would be passing through the tissue.

For ultrasound scanning, the wave is detected at locations adjacent to and/or spaced from the focal region for the ARFI pushing pulse. To detect tissue response to waves in a region of interest, transmissions are made to the region, and detection is performed in the region. These other transmissions are for detecting the waves or displacement rather than causing the wave or displacement. The transmissions for detection may have lower power and/or short pulses (e.g., 1-5 carrier cycles) and use the same or different scan line as the ARFI beam. The transmissions for detection may have a wider beam profile along at least one dimension, such as laterally, for simultaneously forming receive samples along a plurality of scan lines.

The ARFI transmit beam is not used for receiving echoes. The frequency of the tracking waveforms used for transmit and the frequency for receive are independent of the frequencies used for the ARFI beam. For example, the ARFI has a 1-3 MHz chirp while the tracking beams are B-mode beams with a center transmit frequency of 1.5 MHz and a receive frequency of 1.5 MHz or 3 MHz harmonic. Since the ARFI is not used for receiving, the signal from the ARFI does not or has limited interference with the receive signals for tracking.

The wave or displacement may be monitored in one, two, or more directions. A region of interest is monitored to detect the wave. The region of interest is any size. Since the focal region is extended using the swept focal positions and/or frequency sweep, the monitoring may be over a greater depth, lateral range, area, or volume. Waves are generated along the focus. For the axially extended focus in one example, an area of 4 cm in depth and 6 mm in azimuth may be monitored. Laterally spaced locations are monitored for each depth independently. The displacements are tracked at each of a plurality of laterally spaced locations for each depth. The tracking is performed without combining the information over a range of depths. This is possible since sufficient intensity of pushing is applied over the axial extent, allowing for ARFI imaging with greater depth resolution.

The detection region is monitored by ultrasound. The monitoring is performed for any number of scan lines. For example, four, eight, or more receive beams are formed in response to each monitoring transmission. After transmitting the frequency swept ARFI excitation to generate the wave or displacement, B-mode transmissions are performed repetitively along one or more transmit scan lines and receptions are performed along corresponding receive scan lines. In other embodiments, only a single receive beam or other numbers of receive beams are formed in response to each transmission. Some of the ultrasound data, such as at the beginning or end of the repetitions, may not be responsive to the wave or displacement.

An image processor calculates the displacements from the ultrasound scan data (e.g., beamformed samples or B-mode detected data). The tissue moves between two scans. The data of one scan is translated in one, two, or three dimensions relative to the data in the other scan. For each possible relative position, an amount of similarity is calculated for data around a location. The amount of similarity is determined with correlation, such as a cross-correlation. A minimum sum of absolute differences or other function may be used. The spatial offset with the highest or sufficient correlation indicates the amount and direction of displacement for a given location. In other embodiments, a phase offset of data received from different times is calculated. The phase offset indicates the amount of displacement. In yet other embodiments, data representing a line (e.g., axial) at different times is correlated to determine a shift for each of a plurality of depths along the line.

Displacements are determined for a given location at different times, such associated with sequential scans. The displacement is determined with respect to an initial or reference frame of scan data (i.e., cumulative displacement). Alternatively, the displacement is determined from the immediately prior frame of scan data, such assigning the previous frame as the reference on an ongoing basis (i.e., incremental displacement). The temporal profile for a given location indicates displacement caused by the wave over time.

Where the focal region extends sufficiently for the desired measurements, a single ARFI pushing pulse is used. Where a broader region of interest exists despite the time-varying focus, the acts 30-36 may be repeated. The transmissions and receptions for displacement detection are interleaved with ARFI beams to scan different regions of tissue. To monitor a larger region, acts 30-36 are repeated for other locations. For each receive beam location, a time profile of motion information (i.e., displacements) is provided. A separate time profile is provided for each axial depth and/or lateral location.

The displacement information, with or without a time profile, is used to determine a characteristic of the tissue. The characteristic is determined at each location. Any characteristic may be determined, such as an elasticity, strain, shear velocity, longitudinal wave velocity, modulus, or other viscoelastic property. The displacements themselves may be used to represent the tissue, such as the magnitude of the displacement.

In act 38, an image is generated. The image represents the tissue characteristic or property. The image is a function of the displacements. Using the displacements themselves or a characteristic derived from the displacements (e.g., shear modulus or velocity), information to be displayed is calculated. For example, a numerical or textual indication of the property may be displayed. In other embodiments, a plot and/or fit line and slope value are output. For example, displacement over time is displayed for each of one or more locations. The viscoelastic property is communicated to the user in the image. The image may be a graph, such as a plot of values as a function of location.

The image may include a one, two, or three-dimensional representation of the property, displacement, or other wave information as a function of space or location. For example, the shear velocity throughout a region is displayed. Shear velocity values modulate color for pixels in a region in a gray-scale modulated B-mode image. The image may represent displacement information, such as shear or moduli (e.g., the shear moduli) for different locations. The display grid may be different from the scan grid and/or grid for which displacements are calculated. Color, brightness, luminance, hue, or other characteristic of pixels is modulated as a function of the information derived from the displacements.

In other embodiments, the displacements are used for shear wave velocity imaging. The distribution of shear velocities in a two or three-dimensional region are determined and mapped to image values. In another embodiment, shear wave velocity point quantification is performed. The value of the shear wave velocity at a location is displayed as text or a numerical value.

In one embodiment, the image is a function of displacements from different depths. Using one, two, or three-dimensional imaging, the different locations of tissue represented in the image include different depths. For numerical or textual information, the displacements from different depths are used to derive the value or values for different depths. Due to the swept focus of the ARFI beam, displacement at different depths may be detected. The displacement for different lateral positions is detected. By extending the focus for the ARFI beams, more locations in an area or volume may be monitored and used for imaging. By using the frequency sweep, the signal-to-noise ratio for the locations is better than without the frequency sweep. A larger region may be sampled and/or the determined tissue characteristic is more accurate than without the frequency sweep. The intensity as a function of depth for the ARFI may be more uniform using the frequency sweep.

FIG. 6 shows one embodiment of a system 10 for frequency sweep in ARFI scanning. Ultrasound generates tissue displacement, such as through creation of a shear or longitudinal wave, and scan data responsive to the tissue responding to the displacement is used to determine a property. For increased region size for measuring displacement for a given ARFI transmit and/or better signal-to-noise ratio for the measurement locations, the ARFI is transmitted with a frequency sweep. Further improvement is provided by focusing different frequencies to different depths.

The system 10 is a medical diagnostic ultrasound imaging system. In alternative embodiments, the system 10 is a personal computer, workstation, PACS station, or other arrangement at a same location or distributed over a network for real-time or post acquisition imaging. Data from a beamformer-performed scan is available through a computer network or memory for processing by the computer or other processing device.

The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted designation of a region of interest for which information is to be obtained or for entry of an application, type of tissue, and/or setting of rates of change in frequency and/or focal location.

The transmit beamformer 12 is an ultrasound transmitter, memory, pulser, waveform generator, analog circuit, digital circuit, or combinations thereof. The transmit beamformer 12 is configured to generate waveforms for a plurality of channels with different or relative amplitudes, delays, and/or phasing. The waveforms include frequency variation over time. The frequency is swept or varied linearly or non-linearly from the start to the end or during a portion of the continuous waveform. For a given ARFI (e.g., 100-1000 cycles), the frequency (e.g., center frequency and/or band) of the waveform changes. This frequency variation is performed for all or a sub-set of the channels of the transmit beamformer 12.

In one embodiment, the waveforms are generated and applied to a transducer array with a time varying focus. For example, the relative phasing varies over time during the generation of the transmit beam. The waveforms of each channel incorporate the phase variation, resulting in an ARFI pulse or beam with swept focus or multiple focal locations. In correspondence with the frequency variation, different frequencies are focused to different depths or locations. For example, 1 MHz is focused at 10 cm, 3 MHz is focused at 3 cm, and other center frequencies are linearly mapped to locations along a line from 3 cm to 10 cm between 3 MHz and 1 MHz. Due to differences in attenuation by frequency, higher frequencies are focused to focal zones closer to a transducer 14 and lower frequencies focused to focal zones further from the transducer 14. Alternatively, higher frequencies may be focused further than lower frequencies.

The frequency range used for the sweep is adjustable. The attenuation and/or absorption of the tissue being examined may be used to set the frequency range. For example, liver tissue has different attenuation than breast tissue, so different frequencies and resulting range of the sweep are different for the different types of tissue.

The position and size of the region of interest may determine the frequency range. The size and position determine the locations being scanned. Due to attenuation, the frequency used for the deepest locations may be lower than the frequency used for the closest locations. Higher frequencies are desired for resolution, but attenuation limits the frequencies that propagate to the deeper locations.

The frequencies used (e.g., the frequency range) are independent of the speed of sound. Rather than a frequency sweep where the slope of the frequency over time is based on the speed of sound, the frequency sweep may be independent of the speed of sound. Where signals are received for echoes from the transmission, the dynamic receive focusing results in the transmit frequency sweep having frequencies focused at different depths having to match the dynamic focusing, which occurs at the speed of sound. Since there is no receive operation performed for the ARFI, the frequencies and corresponding focal locations may change at any rate. The rates of change of frequency and focal location are adjustable, such as user settable, settable based on application (e.g., tissue type), and/or setting based on region size and position.

In another embodiment for time varying focus, the transmit beamformer 12 include phase rotators 13 in each channel. Each phase rotator 13 is controlled to apply a phase at a time to a generated waveform or a waveform being generated. The phase rotators 13 of the channels of the transmit beamformer 12 are configured to apply different phase profiles across the aperture of the transducer 14 over time and/or to the same ongoing waveforms. The resulting waveforms are generated by the transmit beamformer 12 for creating an ARFI pulse. The phase rotators 13 respond to changes in phase as needed to sweep the focus during a single transmit beam. The focus is shifted laterally, axially, or both, such as creating a line of focal points over time in a same transmit beam.

In another embodiment, the waveform generators of the transmit beamformer 12 (e.g., pulsers or memory with digital-to-analog converters) generate the waveforms for the channels with the relative delay or phasing as part of the waveform. For example, the Kronecker delta function is used as described above for equation 6 to implement the time varying focus with the frequency sweep.

The transmit beamformer 12 connects with the transducer 14, such as through a transmit/receive switch. Upon transmission of acoustic waves from the transducer 14 in response to the generated waveforms, one or more beams are formed during a given transmit event. At least one beam is an ARFI pulse with a frequency sweep with or without a swept focus.

For scanning tissue displacement, a sequence of other transmit beams are generated after the ARFI is transmitted. The sequence of transmit beams scans a one, two or three-dimensional region. Sector, Vector®, linear, or other scan formats may be used. The same region is scanned multiple times. The scanning by the transmit beamformer 12 occurs after transmission of the ARFI pulse. The same elements of the transducer 14 are used for both scanning and displacing tissue, but different elements, transducers, and/or beamformers may be used.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms and connects with the receive beamformer 16 for converting acoustic echoes into electrical receive signals. The transducer 14 transmits the ARFI. The transmit beam of the ARFI is focused at a tissue region or location of interest in the patient. The acoustic waveform is generated in response to applying the electrical waveforms to the transducer elements. The ARFI causes tissue displacement, either directly or through generation of a wave (e.g., shear wave).

For scanning with ultrasound to detect displacement (tracking), the transducer 14 transmits acoustic energy based on further waveforms from the transmit beamformer 12 and receives echoes. Receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection. Dynamic focusing on receive may be provided. The receive beamformer 16 outputs data representing spatial locations using the received acoustic signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or another band.

The receive beamformer 16 outputs beam summed data representing spatial locations. Data for a single location, locations along a line, locations for an area, or locations for a volume are output. The data may be for different purposes. For example, different scans are performed for B-mode or tissue data than for shear wave detection. Alternatively, the scan for B-mode imaging is used for determining tissue displacements. The receive beamformer 16 outputs data representing spatial locations as a function of received acoustic signals responsive to motion of the tissue due to the ARFI. The receive beamformer 16 does not operate while direct echoes from the ARFI impinge on the transducer 14, so the receive beamformer 16 is configured to output the data without acoustic echoes from the ARFI.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information from beamformed ultrasound samples.

In one embodiment, the processor 18 includes one or more detectors and a separate processor. The separate processor is a control processor, general processor, digital signal processor, graphics processing unit, application specific integrated circuit, field programmable gate array, network, server, group of processors, data path, combinations thereof or other now known or later developed device for determining displacement and/or calculating tissue properties. The processor 18 is configured by software and/or hardware to perform the acts.

In one embodiment, the processor 18 estimates tissue displacement over time as a function of the output data from the receive beamformer 16. The displacements are estimated as a profile or data representing a curve of magnitude of displacement as a function of time. The displacement profile may be obtained by correlating or otherwise determining level of similarity between reference data and data obtained to represent the tissue at a different time.

The processor 18 is configured to calculate tissue characteristics form the displacements of the tissue over time. For example, a shear velocity is calculated from the displacement over time. The amount of displacement divided by the time provides velocity. In one embodiment, the processor 18 calculates viscosity and/or modulus. The processor 18 may calculate other properties, such as strain or elasticity. In yet other embodiments, the processor 18 determines the maximum displacement or other characteristic of displacement or the displacement profile as the characteristic.

The processor 18 generates and outputs image or display values mapped from the property to the display 20. For example, the shear modulus or other value is determined. A text or numerical indication of the property is displayed to the user. A graph of the property over time may be displayed.

In one embodiment, the property is displayed as a function of location. Displacements for a limited number of locations are available in response to an ARFI pulse with a single focus. With a swept focus for the ARFI pulse, displacements for a larger number of locations and respective larger linear, area, or volume extent are available. With a frequency sweep, better signal-to-noise is provided for the locations, allowing a larger region to be used for a single ARFI. Values, graphs, and/or tissue representations may be displayed using the displacements at different locations. By using the swept focus as compared to a single focus for the ARFI pulse, a same number of locations may be monitored with fewer ARFI pulse transmissions for quasi-real-time (e.g., 5-19 Hz) imaging. By using the swept focus as compared to a single focus for the ARFI pulse, greater spatial resolution for displacements and corresponding tissue characteristics may be provided. By using the frequency sweep, a more uniform wave generation may be provided, resulting in better signal-to-noise ratio than using a swept focus without a frequency sweep. The estimates of displacement are more likely accurate due to the better signal-to-noise ratio, so provide better information for diagnosis, prognosis, and/or treatment to the physician.

For a representation of the tissue, the magnitude of the tissue characteristic modulates the color, hue, brightness, and/or other display characteristic for different pixels representing a tissue region. The processor 18 determines a pixel value (e.g., RGB) or a scalar value converted to a pixel value. The image is generated as the scalar or pixel values. The image may be output to a video processor, look-up table, color map, or directly to the display 20.

The processor 18 and the transmit beamformer 12 operate pursuant to instructions stored in the memory 22 or another memory. The instructions configure the processor 18 and/or the transmit beamformer 12 for operation by being loaded into a controller, by causing loading of a table of values (e.g., phase profile table), and/or by being executed. The transmit beamformer 12 is configured by the instructions to cause generation of an ARFI beam with a frequency sweep with or without a swept focus. The processor 18 is programmed for measuring tissue displacement and generating an image.

The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 displays one or more images representing the tissue characteristic or other information derived from displacements. As an example, a two-dimensional image or three-dimensional representation of displacement or tissue characteristics as a function of location is displayed. Alternatively or additionally, the image is a graph, a number, or text representation of a value or graph. For example, a shear velocity, shear modulus, strain, elasticity or other value or graph is displayed as the image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for swept frequency in acoustic radiation force impulse scanning by an ultrasound system, the method comprising:
   transmitting, by the ultrasound system and from an ultrasound transducer, a transmit beam with a frequency sweep as an acoustic radiation force impulse where different frequencies of the transmit beam are focused at different depths;
   tracking, by the ultrasound system using the ultrasound transducer, displacements of tissue at different depths, the displacement being in response to the acoustic radiation force impulse; and
   generating an image, the image being a function of the displacement of the tissue at the different depths.

2. The method of claim 1 wherein transmitting comprises transmitting the transmit beam with the frequency sweep and a time varying focal position.

3. The method of claim 1 wherein transmitting comprises generating the transmit beam with element waveforms that are continuous over time.

4. The method of claim 3 wherein transmitting comprises transmitting with the acoustic radiation force impulse having one hundred or more cycles.

5. The method of claim 1 wherein transmitting comprises transmitting with a change in the frequencies over time being adjustable.

6. The method of claim 5 further comprising receiving user input, a setting for the change being based on the input from the user.

7. The method of claim 5 wherein transmitting comprises transmitting with the change different than based a speed of sound, and wherein tracking comprises tracking without receiving echoes from the transmit beam.

8. The method of claim 5 wherein transmitting comprises transmitting with setting of the change being a rate of change set based on a type of tissue, a size of a region of interest, and a position of the region of interest.

9. The method of claim 2 wherein transmitting comprises transmitting with a rate of change in the frequencies over time being adjustable and a rate of change of the time varying focus being adjustable.

10. The method of claim 2 wherein transmitting comprises transmitting with the time varying focal position comprises generating element waveforms as a function of a Kronecker delta function of a depth range and with a sin function of a frequency range.

11. The method of claim 1 wherein transmitting comprises transmitting the transmit beam with an aperture size that is time varying.

12. The method of claim 1 wherein tracking comprises tracking the displacements laterally and independently at each of the different depths.

13. The method of claim 1 wherein tracking comprises tracking the displacements axially at each of the different depths and along at least eight scan lines.

14. The method of claim 1 wherein generating comprises generating the image with pixels modulated as a function of the tracked displacements in a two or three-dimensional field.

15. A system for swept frequency in acoustic radiation force impulse scanning, the system comprising:
an ultrasound transducer for transmitting an acoustic radiation force impulse in a patient;
a transmit beamformer configured to generate waveforms for the acoustic radiation force impulse, the waveforms resulting in the acoustic radiation force impulse having higher frequencies focused to focal zones closer to a transducer and lower frequencies focused to focal zones further from the transducer;
a receive beamformer configured to output data representing spatial locations as a function of received acoustic signals responsive to motion of the tissue due to the acoustic radiation force impulse;
a processor configured to estimate displacement of the tissue in the patient over time as a function of the output data; and
a display operable to display an image, the image being a function of the displacement.

16. The system of claim 15 wherein the transmit beamformer is configured to provide the higher and lower frequencies as a function of a frequency range, the frequency range being a function of an attenuation of the tissue.

17. The system of claim 15 wherein the receive beamformer is configured to output the data without acoustic echoes from the acoustic radiation force impulse and wherein the transmit beamformer is configured to provide the higher and lower frequencies independent of a speed of sound.

18. The system of claim 15 wherein the transmit beamformer is configured to provide the higher and lower frequencies based on a setting for a rate of change of frequency, to generate the waveforms for a time varying focal position of the acoustic radiation force impulse, the time varying focal position based on a setting for a rate of change of focus.

19. A method for swept frequency in acoustic radiation force impulse scanning by an ultrasound system, the method comprising:
transmitting, by the ultrasound system and from an ultrasound transducer, a transmit beam as an acoustic radiation force impulse where different frequencies of the transmit beam are focused at different depths and having a time varying focal position;
tracking, by the ultrasound system using the ultrasound transducer, displacements of tissue at different depths, the displacement being in response to the acoustic radiation force impulse; and
generating an image, the image being a function of the displacement of the tissue at the different depths.

20. The method of claim 19 wherein transmitting comprises transmitting with an adjustable rate of change of focus for the time varying focal position and an adjustable rate of change of frequency for the different frequencies to the different depths.

* * * * *